United States Patent [19]

Murakata et al.

[11] Patent Number: 5,344,926
[45] Date of Patent: Sep. 6, 1994

[54] PROCESS FOR PRODUCING STAUROSPORINE DERIVATIVES

[75] Inventors: Chikara Murakata, Hachioji; Toshimitsu Takiguchi, Gotenba; Shigeo Katsumata, Mishima; Akira Mihara, Machida; Keiichi Takahashi, Susono; Hiromitsu Saito, Mishima; Shiro Akinaga, Shizuoka; Masami Okabe, Mishima; Yutaka Saito, Machida, all of Japan

[73] Assignee: Kyowa Hakko Kogyo Co., Ltd., Tokyo, Japan

[21] Appl. No.: 79,560

[22] Filed: Jun. 22, 1993

[30] Foreign Application Priority Data

Jun. 22, 1992 [JP] Japan .................. 4-162813
Jun. 22, 1992 [JP] Japan .................. 4-162814

[51] Int. Cl.$^5$ .......................... C07D 498/22
[52] U.S. Cl. ...................... 540/545; 540/546
[58] Field of Search .............. 540/545; 435/119

[56] References Cited

U.S. PATENT DOCUMENTS

| | | | |
|---|---|---|---|
| 4,923,986 | 5/1990 | Murakata et al. | 540/545 |
| 4,935,415 | 6/1990 | Nakano et al. | 540/545 |
| 4,973,552 | 11/1990 | Schroeder et al. | 435/898 |
| 5,015,578 | 5/1991 | Schroeder et al. | 435/119 |

FOREIGN PATENT DOCUMENTS

| | | |
|---|---|---|
| 0383919 | 1/1989 | European Pat. Off. . |
| 0323171 | 7/1989 | European Pat. Off. ............ 540/545 |
| 0508792 | 4/1992 | European Pat. Off. . |
| 89/07105 | 8/1989 | Int'l Pat. Institute . |
| 91/09034 | 6/1991 | Int'l Pat. Institute . |
| WO/9109034 | 12/1990 | PCT Int'l Appl. . |

OTHER PUBLICATIONS

Takahashi et al. J. Antibiotics, Dec. 1987, pp. 1782–1784.
Journal of Antibiotics, 42, 564 (1989).
Journal of Antibiotics, vol. 42, No. 4, 1989, pp. 571–576, I. Takahashi et al., "UCN-01 and UCN-02, New Selective Inhibitors of Protein Kinase C. II. Purification,, Physico-Chemical Properties, Structural Determination and Biological Activities".

Primary Examiner—Mukund J. Shah
Assistant Examiner—Pavanaram K. Sripada
Attorney, Agent, or Firm—Antonelli, Terry, Stout & Kraus

[57] ABSTRACT

Disclosed is a process for producing a staurosporine derivative represented by Formula (I): Q is defined as in specification:

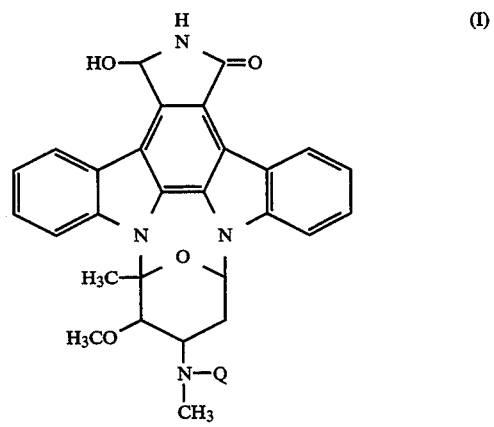

The staurosporine derivative (I-1) possesses selective protein kinase C-inhibitory and cell growth-inhibiting activities, and platelet-increasing activity.

4 Claims, No Drawings

PROCESS FOR PRODUCING STAUROSPORINE DERIVATIVES

BACKGROUND OF THE INVENTION

The present invention relates to a process for producing staurosporine derivatives. The present invention further relates to a novel staurosporine derivative.

Staurosporine is a known anti-tumor agent having the following formula:

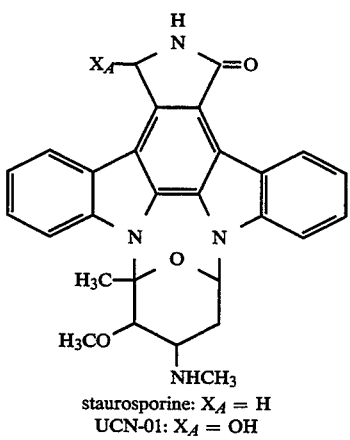

staurosporine: $X_A$ = H
UCN-01: $X_A$ = OH

As the staurosporine derivatives, UCN-01 having anti-tumor activity is known (EP-A-238011, U.S. Pat. No. 4,935,415). Further, stereoisomers of UCN-01 are disclosed in Journal of Antibiotics, 42, 564 (1989); and derivatives of UCN-01, are disclosed in WO89/07105.

The following two methods have heretofore been known, for producing UCN-01:

(1) A fermentation method which comprises culturing a microorganism belonging to the genus Streptomyces and having an ability to produce UCN-01 in a medium, and recovering UCN-01 therefrom (U.S. Pat. No. 4,935,415).

(2) A chemically synthetic method which comprises oxidizing Compound (A) represented by the formula (A), which is easily produced from staurosporine with lead tetraacetate in acetic acid and removing the protecting group by the catalytic reduction of the oxidized product of Compound (A) to afford UCN-01 (European Publication No. 383,919).

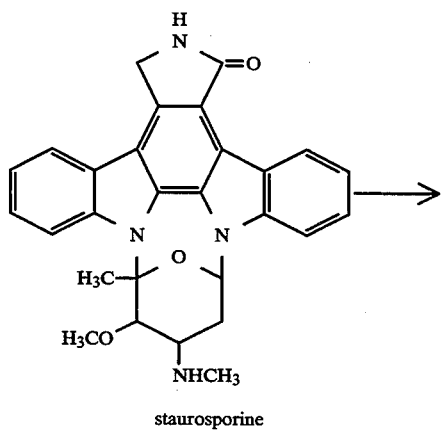

staurosporine

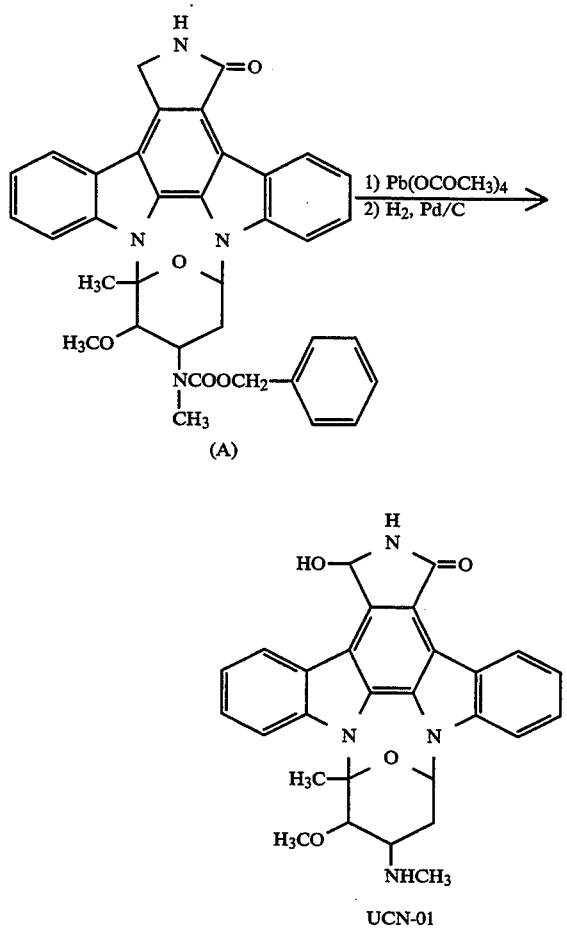

However, the potency in the fermentation method is low; and the yield in the chemically synthetic method is low since the method involves three steps for obtaining UCN-01.

SUMMARY OF THE INVENTION

The staurosporine derivatives as used herein mean UCN-01 and UCN-01 derivatives.

An object of the present invention is to provide a process for efficiently and simply producing UCN-01 and UCN-01 derivatives.

Another object of the present invention is to provide a novel UCN-01 derivative. The novel UCN-01 derivative possesses selective protein kinase C-inhibitory and cell growth-inhibitory activities, and platelet-increasing activity.

In accordance with the present invention, there is provided a process for producing staurosporine derivatives [hereafter referred to as Compound (I); compounds having other formulae numbers are similarly referred to] represented by Formula (I):

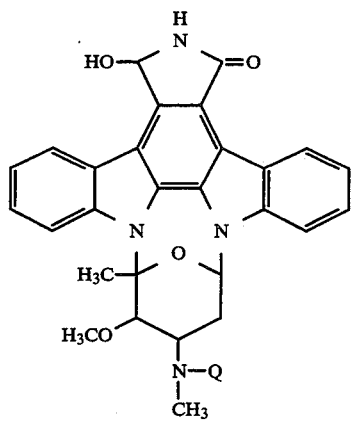

(I)

wherein:
Q represents hydrogen or —X—(CH₂)ₘ—Y—(CH₂)ₙ—Z wherein X represents a single bond or —CO—

Y represents a single bond or —CH(OH)—

Z represents hydroxy, OCON R¹ R², in which each of R¹ and R² independently represents hydrogen or lower alkyl, or R¹ and R², combined together with the nitrogen atom adjacent thereto, form a heterocyclic group carboxyl, N R³ R⁴, in which each of R³ and R⁴ independently represents hydrogen or lower alkyl, or R³ and R⁴, combined together with the nitrogen atom adjacent thereto, form a heterocyclic group or, substituted or unsubstituted aryl, each of m and n independently represents an integer of from 0 to 6, or a pharmaceutically acceptable salt thereof, which comprises oxidizing a compound represented by Formula (II):

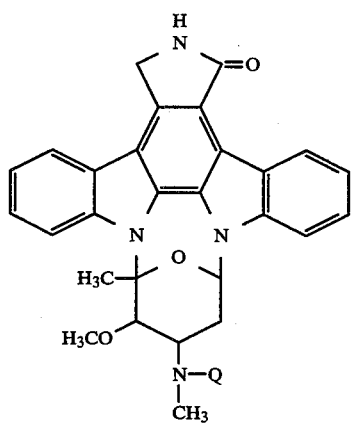

(II)

wherein Q has the same meaning as previously defined, with a mixture of dimethylsulfoxide (DMSO) and an aqueous alkaline solution.

Furthermore, in accordance with the present invention, there is provided a novel UCN-01 derivative represented by the formula (I-1):

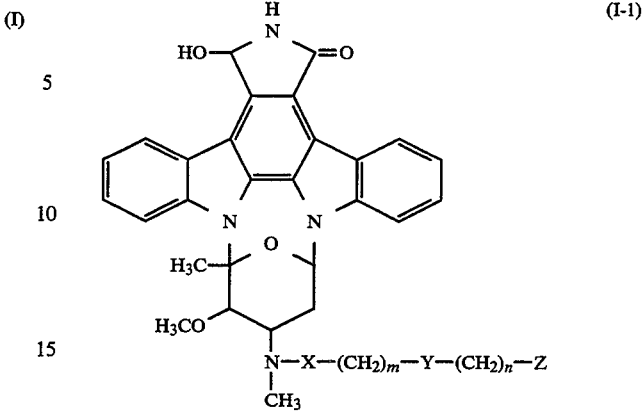

(I-1)

wherein:
X represents a single bond or —CO—
Y represents a single bond or —CH(OH)—
Z represents hydroxy, O C O N R¹ R², in which each of R¹ and R² independently represents hydrogen or lower alkyl, or R¹ and R², combined together with the nitrogen atom adjacent thereto, form a heterocyclic group carboxyl, N R³ R⁴, in which each of R³ and R⁴ independently represents hydrogen or lower alkyl, or R³ and R⁴, combined together with the nitrogen atom adjacent thereto, form a heterocyclic group or, substituted or unsubstituted aryl,
each of m and n independently represents an integer of from 0 to 6,
or a pharmaceutically acceptable salt thereof.

DETAILED DESCRIPTION OF THE INVENTION

In the definition of the groups in formulae (I) and (I-1), the lower alkyl means a straight or branched alkyl having 1 to 6 carbon atoms, such as methyl, ethyl, propyl, isopropyl, butyl, tert-butyl, pentyl and hexyl. The heterocyclic group to be formed by R¹ and R², or by R³ and R₄, along with the nitrogen atom adjacent thereto includes, for example, pyrrolidinyl, imidazolidinyl, pyrazolidinyl, piperidino, morpholino, piperazinyl, N-methylpiperazinyl, indolinyl and isoindolinyl.

The substituted or unsubstituted aryl includes, for example, phenyl and naphthyl, which is optionally substituted with 1 to 3 substituents independently selected from the group consisting of lower alkyl, lower alkoxy, amino, halogen and nitro. The alkyl and the alkyl moiety in the lower alkoxy have the same meaning as defined above. The halogen includes fluorine, chlorine, bromine and iodine.

As the pharmaceutically acceptable salt of Compound (I), mention may be made of an acid addition salt such as hydrochloride, hydrobromide, sulfate, formate, acetate, benzoate, maleate, fumarate, succinate, tartrate, citrate, oxalate, methanesulfonate, toluenesulfonate, aspartate and glutamate; an ammonium salt; an alkali metal salt such as lithium salt, sodium salt and potassium salt; an alkaline earth metal salt such as calcium salt and magnesium salt; an organic amine addition salt such as triethylamine salt, N-methylmorpholine salt, piperidine salt and dicyclohexylamine salt; an amino acid addition salt such as arginine salt and lysine salt.

As an alkali source suitable for the aqueous alkaline solution for use in the process for producing UCN-01 and UCN-01 derivatives, mention may be made of hydroxides of alkali metals such as lithium, sodium and potassium, and hydroxides of alkaline earth metals such as calcium and magnesium. Preferably, sodium hydroxide and potassium hydroxide are used. The concentration of the aqueous alkaline solution is in the range of 0.1N to 10N.

The mixing ratio of DMSO with the aqueous alkaline solution is from 2:1 to 10:1. The mixture may be used in an amount of from 5 to 100 ml per gram of Compound (II). The oxidizing reaction is generally carried out at a temperature of from 0° to 50° C., and the reaction time is in the range of from 1 to 24 hours.

After completion of the reaction, the reaction mixture is extracted with an organic solvent, and the organic layer is subjected to purification by, for example, chromatography or the like to isolate and obtain the intended Compound (I).

Out of Compound (II), staurosporine which is Compound (II) wherein Q is hydrogen, is commercially available from Kyowa Medex Co., Ltd., Japan. The process for producing Compound (II-1) which is Compound (II) wherein Q is $-X-(CH_2)_m-Y-(CH_2)_n-Z$ is given below.

Out of Compound (II-1), Compound (II-1-1), which is Compound (II-1) where X is a single bond is produced by the following reaction step.

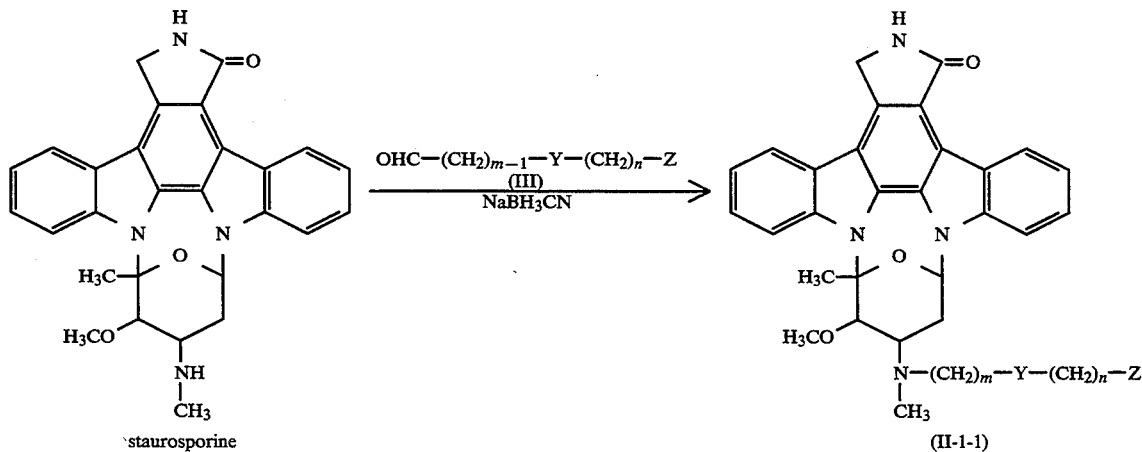

wherein m, n, Y and Z have the same meanings as defined above.

Staurosporine is reacted with Compound (III) having the formula $OHC-(CH_2)_{m-1}-Y-(CH_2)_n-Z$ (in which m, n, Y and Z have the same meanings as defined above) in an inert solvent, such as tetrahydrofuran (THF), at a pH of 5 to 6 in the presence of a suitable reducing agent such as sodium cyanoborohydride to obtain Compound (II-1-1). The reducing agent and Compound (III) are individually used in an amount of from 2 to 5 equivalents based on staurosporine. The reaction is carried out at 0° to 50° C. and completed in 1 to 5 hours.

Out of Compound (II-1), Compound (II-1-2), which is Compound (II-1) where X is -CO- is produced by the following reaction step.

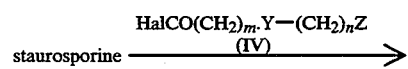
$$\xrightarrow{HalCO(CH_2)_m\text{-}Y-(CH_2)_nZ \atop (IV)}$$

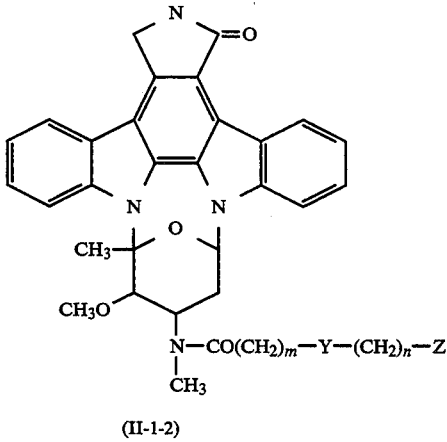

where Hal represents chlorine, bromine or iodine, and m, n, Y and Z have the same meanings as defined above.

Staurosporine is reacted with Compound (IV) having the formula $HalCO-(CH_2)_m-Y-(CH_2)_n-Z$ (in which Hal, m, n, Y and Z have the same meanings as defined above) in the presence of a suitable base such as pyridine and triethylamine, optionally in a solvent such as methylene chloride to obtain Compound (II-1-2). Compound (IV) is used in an amount of from 1 to 5 equivalents based on staurosporine. The reaction is carried out generally at 0° to 50° C. and completed in 0.5 to 6 hours.

Out of Compound (II-1), Compound (II-1-3), which is Compound (II-1) where Z is $NR^3R^4$, is produced by the following reaction step.

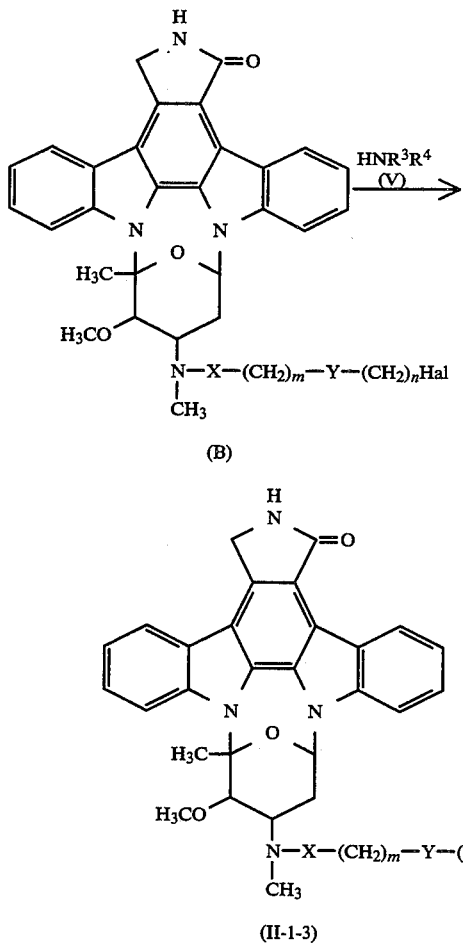

(B)

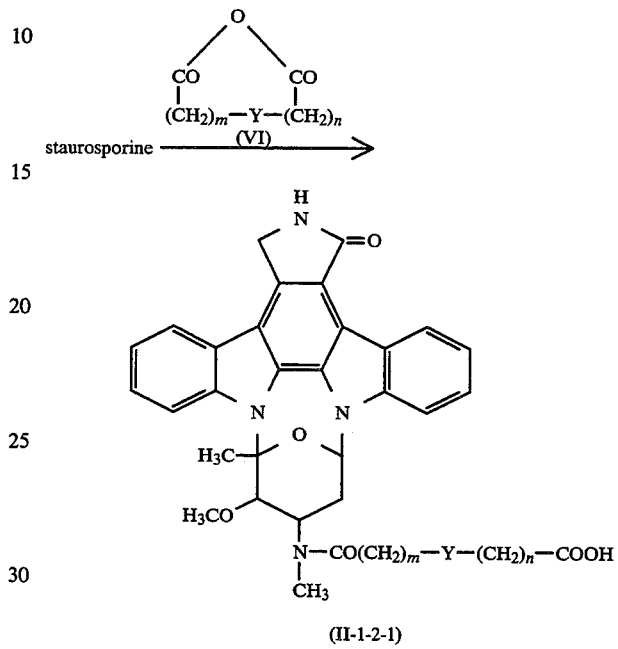

(V) are individually used in an amount of from 2 to 6 equivalents based on Compound (B). The reaction is carried out at 0° to 50° C. and completed in 1 to 24 hours.

Out of Compound (II-1-2), Compound (II-1-2-1) which is Compound (II-1-2) where Z is COOH may also be produced by the following reaction step.

(II-1-3)

where Hal, m, n, X, Y, $R^3$ and $R^4$ have the same meanings as defined above.

Compound (B) can be obtained by reacting staurosporine with Compound (III) or (IV) where Z is Hal, in accordance with the process for producing Compound (II-1-1) or (II-1-2) as defined above. Compound (B) is reacted with Compound (V) represented by $HNR^3R^4$ (where $R^3$ and $R^4$ have the same meanings as defined above) in an inert solvent such as dimethylformamide (DMF) in the presence of a base such as triethylamine, to obtain Compound (II-1-3). The base and Compound (II-1-2-1)

wherein m, n and Y have the same meanings as defined above.

Compound (II-1-2-1) can be obtained by reacting staurosporine with Compound (VI), in an inert solvent such as DMF, in the presence of a base such as dimethylaminopyridine. The base is used in an amount of from 0.5 to 1 equivalent based on staurosporine; and Compound (VI) is used in an amount of from 2 to 3 equivalents based on staurosporine. The reaction is carried out at 0° to 50° C. and completed in 3 to 5 hours.

Compound (II-1-a) which consists of Compound (II-1) where Z is $OCONR^1R^2$ and Compound (II-1-2) where Z is $NR^3R^4$, m and n are both 0 and Y is a single bond, may also be produced by the following reaction step.

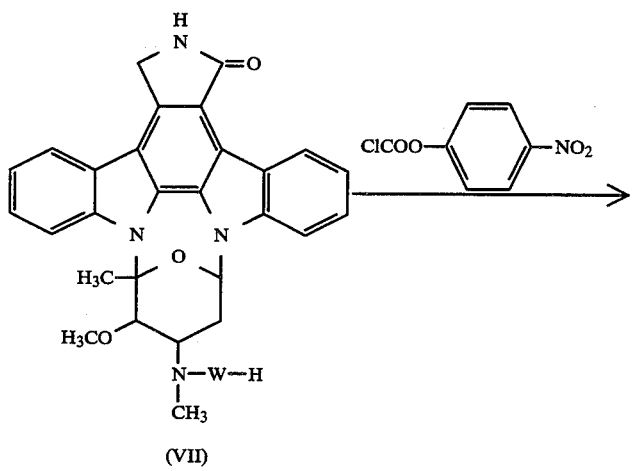

(VII)

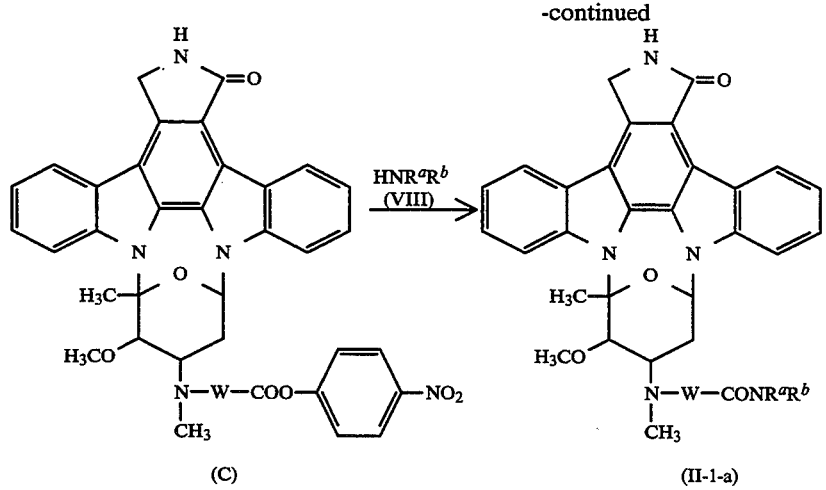

where $NR^aR^b$ has the same meaning as $NR^1R^2$ as defined above; and W represents $-X-(CH_2)_m-Y-(CH_2)_n-O$ (in which m, n and Y have the same meanings as defined above) or a single bond.

Compound (VII), which is Compound (II-1) where Z is hydroxy, is reacted with nitrophenyl chlorocarbonate in an inert solvent such as THF and chloroform, in the presence of a base such as triethylamine to obtain Compound (C). The base and nitrophenyl chlorocarbonate are individually used in an amount of from 1 to 5 equivalents based on Compound (VII). The reaction is carried out at 0° to 50° C. and completed in 2 to 24 hours.

Compound (C) is reacted with Compound (VIII) having the formula $HNR^aR^b$ (in which $NR^aR^b$ has the same meaning as defined above) in an inert solvent such as chloroform and DMF in the presence of a base such as triethylamine to obtain Compound (II-1-a). The base and Compound (VIII) are individually used in an amount of from 2 to 6 equivalents based on Compound (C). The reaction is carried out at 0° to 80° C. and completed in 1 to 24 hours.

Out of Compound (II-1), those where Z is an aryl substituted by amino, can be obtained by catalytically reducing the corresponding compound where the corresponding substituent in the substituted aryl is nitro, with 10% palladium catalyst (Pd/C) in an inert solvent such as DMF. The reaction is carried out generally at 0° to 50° C. and completed in 2 to 5 hours.

The intermediates and objective compounds in the respective methods described above can be isolated and purified by purification methods conventionally used in organic synthetic chemistry, for example, filtration, extraction, washing, drying, concentration, recrystallization, various column chromatographies, etc. Further the intermediates may also be provided in the subsequent reaction, without being particularly purified.

Compound (I) includes stereoisomers of α-form and β-form with respect to stereochemistry. In general, the methods described above often give a mixture of these stereoisomers. Isolation and purification of these stereoisomers can be made in a conventional manner used in organic synthetic chemistry, for example, by column chromatography, recrystallization, etc.

Further, if desired, α- and β-forms may be isomerized from each other. This can be made by treating each isomer in a reflux of, e.g., acetic acid, for 1 to 24 hours, in the presence of an appropriate acid catalyst such as p-toluenesulfonic acid, etc.

In the present invention, Compound (I) includes not only the α/β stereoisomers described above but also all possible stereoisomers and a mixture thereof.

In case that salts of Compound (I) are desired to obtain, when Compound (I) is obtained in the form of a salt, Compound (I) may be purified as it is. Further in case that Compound (I) is obtained in a free form, salts may be formed in a conventional manner.

Furthermore, Compound (I-1) and pharmaceutically acceptable salts thereof may also be present in the form of addition products to water or various solvents; these adducts are also included in the present invention.

Specific examples of Compound (I-1) obtained by various methods are shown in Table 1.

TABLE 1

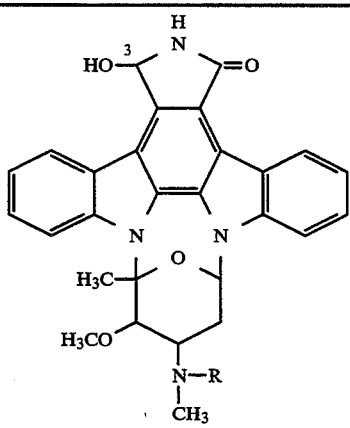

| Compound No. | —R |
|---|---|
| 1 | —(CH₂)₂OH |
| 2 | —CH₂CH(OH)CH₂OH |
| 3 | —(CH₂)₃CO₂H |
| 4 | —(CH₂)₂OCO—N⌒N—CH₃ |
| 5 | —CO(CH₂)₂CO₂Na |
| 6 | —COCH₂—N⌒O |
| 7 | —COCH₂N(CH₃)₂ |

TABLE 1-continued

[Chemical structure diagram showing a polycyclic compound with H, N, HO, O, H3C, H3CO, N-R, CH3 substituents]

| Compound No. | —R |
|---|---|
| 8 | —COCH$_2$—N(piperazine)N—CH$_3$ |
| 9 | —CO—(phenyl with NH$_2$, NH$_2$ substituents) |
| 10 | —CO—N(piperazine)N—CH$_3$ |

These compounds are in the form of a mixture of about 1:1 stereoisomers at the 3-position.

The pharmacological activities of Compound (I-1), were illustrated below.

EXPERIMENTAL EXAMPLE 1

Growth Inhibition Test on HeLa S$_3$ Cells

HaLa S$_3$ cells were suspended in an MEM medium containing 10% fetal calf serum and 2 mM glutamine at a concentration of $3 \times 10^4$ cells/ml, and 0.1 ml of the cell suspension was put into each well of a 96-well microtiter plate.

After culturing at 37° C. overnight in a carbon dioxide gas incubator, 0.05 ml of a test sample appropriately diluted with the medium was added to each well. The cells were further cultured for one hour in the carbon dioxide gas incubator and the culture supernatant was removed. The residue was washed once with a phosphate buffer saline [PBS(-)] and 0.1 ml of a fresh medium was added to each well, and the cells were further incubated at 37° C. for 72 hours in the carbon dioxide gas incubator. After removal of the supernatant, 0.1 ml of culture medium containing 0.02% Neutral Red was added to each well, and the cells were further incubated at 37° C. for one hour in the carbon dioxide gas incubator to stain the cells. After removal of the culture supernatant, each well was washed once with a physiological saline, and the dye was extracted with 0.001N HCl/30% methanol. Absorbance of the extract at 550 nm was measured with a microplate reader. The cell growth inhibition percentage was calculated according to the following formula from the absorbance of the extract of the cells treated with the test compound in various concentrations and that of intact cells.

Cell Growth Inhibition Percentage (%) =

$$100 - \frac{\text{(absorbance of cells treated with test compound)} - \text{(absorbance of cell-free well)}}{\text{(absorbance of intact cells)} - \text{(absorbance of cell-free well)}} \times 100$$

From the cell growth inhibition percentage thus obtained, the concentration of the test compound which inhibits cell growth by 50% (IC$_{50}$) was determined.

The results are shown in Table 2.

TABLE 2

| Compound No. | IC$_{50}$ (μM) |
|---|---|
| 1 | 2.2 |
| 2 | 1.9 |
| 3 | 4.6 |
| 6 | 2.2 |
| 7 | 1.5 |

EXPERIMENTAL EXAMPLE 2

(1) Protein Kinase C Inhibitory Activity

Protein kinase C inhibitory activity (PKC) was measured by the method of Kikkawa, et al. (Journal of Biological Chemistry, 257, 13341 (1982)].

That is, 10 μl of a test solution containing UCN-01, Compound No. 1-α or Compound No. 1-β was added to 250 μl of a solution containing 2.5 μmoles of magnesium acetate, 50 μg of Histone Type IIS (manufactured by Sigma Co., Ltd.), 20 μg of phosphatidyl serine, 0.8 μg of diolein, 25 nmoles of CaCl$_2$, 5 μg of crude enzyme (partically purified from rat brain according to the method of Kikkawa, et al.) and 5 μmoles of Tris-hydrochloride buffer (pH 7.5), followed by incubation at 30° C. for 3 minutes. Then, phosphorylation was initiated by addition of 1.25 nmoles of [γ-$^{32}$p]ATP(5 to $10 \times 10^3$ cpm/nmole), followed by incubation at 30° C. for 3 minutes. The reaction was stopped by adding 25% trichloroacetic acid (TCA), and the reaction solution was filtered through a cellulose acetate membrane (pore size of 0.45 μm) (manufactured by Toyo Filter Paper Co., Ltd.). After the membrane was washed four times with 5% TCA, radioactivity remaining on the membrane was measured. As a control, the same procedure as above was repeated without addition of the test solution and radioactivity was likewise measured. A concentration of the test solution showing 50% inhibition as compared with the control was expressed as IC$_{50}$.

The results are shown in Table 3.

(2) Protein Kinase A Inhibitory Activity

Protein kinase A inhibitory activity (PKA) was measured according to the method of Kuo, et al. [Biochemistry, 64, 1349 (1969)].

That is, 10 μl of a test solution was added to 250 μl of a solution containing 5 μmoles of Tris-hydrochloride buffer (pH 6.8), 2.5 μmoles of magnesium acetate, 100 μg of Histone Type IIS (manufactured by Sigma Co., Ltd.), 0.25 nmoles of C-AMP and 200 μg of crude enzyme (partially purified from calf heart according to the method Kuo, et al.). Subsequent procedures were conducted in a manner similar to the case of measuring protein kinase C inhibitory activity described above to determine $IC_{50}$. The results are shown in Table 3.

TABLE 3

| Test Compound | $IC_{50}$ (ng/ml) | | |
|---|---|---|---|
| | PKC | PKA | PKA/PKC |
| UCN-01 | 2 | 20 | 10 |
| Compound No. 1-α | 2.2 | 260 | 118 |
| Compound No. 1-β | 19 | 370 | 20 |

Compound No. 1-α and Compound No. 1-β have a selective inhibitory activity on protein kinase C, compared with UCN-01.

EXPERIMENTAL EXAMPLE 3

Platelet increasing activity of Compound (I-1) was examined. Compound No. 1-α obtained in Example 13 was suspended in 0.3% carboxymethylcellulose aqueous solution containing 5% Tween 80. 0.2 ml of the suspension was intraperitoneally administered to six Balb/c mice (male, aged 7 weeks) at a dosage of 20 mg/kg once a day for 5 days. The blood (20 μl) was collected from the ophthalmic descending aorta at the times, just before the test compound administration (Day 0), the 7th day (Day 7), the 14th day (Day 14), the 17th day (Day 17) and the 28th day (Day 28). The number of platelets was counted by a microcellcounter. The result is shown in Table 4.

TABLE 4

| mouse | Number of platelets | | | | |
|---|---|---|---|---|---|
| | Day 0 | Day 7 | Day 14 | Day 17 | Day 28 |
| #1 | 81.8 | 128.3 | 113.7 | 115.0 | 117.3 |
| #2 | 89.6 | 119.2 | 122.5 | 113.6 | 123.5 |
| #3 | 75.0 | 130.1 | 118.8 | 111.9 | 119.0 |
| #4 | 89.7 | 153.8 | 145.9 | 159.1 | 113.7 |
| #5 | 97.0 | 141.0 | 121.2 | 137.1 | 105.8 |
| #6 | 86.5 | 140.1 | 101.7 | 125.5 | 125.3 |
| (mean) | 86.6 | 135.4 | 121.1 | 127.0 | 117.4 |
| (standard deviation) | 7.5 | 12.1 | 13.7 | 18.3 | 7.1 |
| relative value (%) | 100 | 156.4 | 139.8 | 146.7 | 135.1 |

The compounds obtained by the present invention which are effective as anti-tumor agent, are used in the form of an injection. They are dissolved in a diluent which is conventionally used in the art, such as a physiological saline solution, or glucose, lactose or mannitol solution for injection. Alternatively, the compounds may be freeze-dried according to the Japanese Pharmacopoeia to give a powder for injection or may be prepared into a powder by adding sodium chloride thereto. In addition, the injection may also contain an auxiliary agent such as polyethylene glycol or HCO-60 (surfactant manufactured by Nikko Chemical Co.), as well as carrier such as ethanol and/or liposome or cyclodextrin. The injections are generally used for intravenous administration, but may also be used for intra-arterial administration, intraperitoneal administration or intrathoracical administration.

Where Compounds (I-1) are used as a peroral drug, they may also be formed into tablets, granules, powder or syrup for oral administration with an appropriate excipient, disintegrator, binder or lubricant in a conventional manner. Further, Compound (I-1) may be mixed with a conventional carrier and formed into suppositories for rectal administration in a conventional manner.

Dosage may appropriately vary according to the administration schedule, the kind of Compound (I-1), and the age and condition of a patient. Administration schedule may also be varied according to the condition of a patient and the dosage. For example, the compounds can be administered in a dose of 0.01 to 20 mg/kg once a day (single administration or cumulative administrations) or intermittently once or three times a day or once three weeks.

Certain embodiments of the invention are illustrated in the following examples.

EXAMPLE 1

100 mg (0.21 mmol) of staurosporine (commercially available from Kyowa Medex Co., Ltd., Japan) was dissolved in a mixture of 4 ml of DMSO and 1 ml of 2N sodium hydroxide. The solution was stirred overnight at room temperature. The reaction solution was diluted with ethyl acetate, washed with water and brine in order, and dried over anhydrous magnesium sulfate. The solvent was evaporated, and the residue was purified by silica gel column chromatography using the elution with 0%, 4%, 6%, and 10% acetone-containing chloroform in order to obtain 60 mg (yield: 59%) of UCN-01.

EXAMPLE 2

The same procedure as described in Example 1 was repeated, except that 0.5N sodium hydroxide was used in place of 2N sodium hydroxide, and 2.2g (yield: 70%) of UCN-01 was obtained from 3.0g of staurosporine.

EXAMPLE 3

300 mg of Compound (e) as obtained in Reference Example 1 was dissolved in 20 ml of DMSO and 6.6 ml of 0.5N sodium hydroxide and stirred overnight at room temperature. The reaction mixture was diluted with THF, washed with brine, and dried over anhydrous sodium sulfate. Then, the solvent was evaporated, and the residue was purified by silica gel column chromatography (eluent: 5/95 methanol/chloroform) to obtain 140 mg (yield: 45%) of Compound No. 1.

$^1$HNMR (DMSO-$d_6$) δ(ppm); 4.25 (s, 1H), 6.84 (dd, 1H, J=3.84, 8.98), 7.28–8.51 (m, 7H), 8.75 (s, 1H), 9.24 (d, 1H, J=8.03) SIMS (m/z); 527 (M+1)+

EXAMPLE 4

The same process as described in Example 3 was repeated except that 96 mg of Compound (f) as obtained in Reference Example 2 was used in place of Compound (e), to obtain 43 mg (yield: 43%) of Compound No. 2.

$^1$HNMR (DMSO-$d_6$) δ(ppm); 7.30–8.52 (m, 7H), 9.25 (d, 1H, J=7.87) SIMS (m/z); 557 (M+1)+

EXAMPLE 5

The same process as described in Example 3 was carried out, except that 400 mg of Compound (g) as obtained in Reference Example 3 was used in place of Compound (e), to obtain 172 mg (yield: 42%) of Compound No. 3.

$^1$HNMR (DMSO-$d_6$) δ(ppm); 1.23–1.59 (m, 2H), 4.24 (s, 1H), 6.43 (s, 2H), 6.82–6.86 (m, 1H), 7.28–8.51 (m, 7H), 8.76, 8.77 (2xs, 1H), 9.24 (d, 1H, J=8.00) SIMS (m/z); 569 (M+1)+

EXAMPLE 6

The same process as described in Example 3 was repeated, except that 74 mg of Compound (h) as obtained in Reference Example 5 was used in place of Compound (e), to obtain 28 mg (yield: 37%) of Compound No. 4.

$^1$HNMR (DMSO-d$_6$) δ(ppm); 4.23 (s, 1H), 7.28–8.50 (m, 7H), 8.75 (s, 1H), 9.23 (d, 1H, J=8.01) SIMS (m/z); 653 (M+1)$^+$

EXAMPLE 7

The same process as described in Example 3 was repeated, except that 450 mg of Compound (i) as obtained in Reference Example 6 was used in place of Compound (e), to obtain 215 mg (yield: 45%) of Compound No. 5.

$^1$HNMR (DMSO-d$_6$) δ(ppm); 4.24, 4.26 (2xbr.s, 1H), 5.01 (m, 1H), 6.45 (br.s, 1H), 6.99–7.03 (m, 1H), 7.28–8.50 (m, 7H), 8.87 (br.s, 1H), 9.23 (d, 1H, J=7.96) SIMS (m/z); 653 (M+1)$^+$

EXAMPLE 8

The same process as described in Example 3 was repeated, except that 150 mg of Compound (j) as obtained in Reference Example 8 was used in place of Compound (e), to obtain 93 mg (yield: 61%) of Compound No. 6.

$^1$HNMR (DMSO-d$_6$) δ(ppm); 2.32, 2.33 (2xs, 3H), 2.88, 2.90 (2xs, 3H), 6.45 (s, 1H), 7.01–7.06 (m, 1H), 7.29–8.50 (m, 7H), 8.81 (s, 1H), 9.23, 9.25 (2xd, 1H, J=7.90) SIMS (m/Z); 610 (M+1)$^+$

EXAMPLE 9

The same process as described in Example 3 was repeated, except that 180 mg of Compound (k) as obtained in Reference Example 9 was used in place to Compound (e), to obtain 104 mg (yield: 56%) of Compound No. 7.

$^1$HNMR (DMSO-d$_6$) δ(ppm); 4.24 (s, 0.33H), 4.27 (s, 0.33H), 4.39 (s, 0.17H), 4.42 (s, 0.17H), 6.44 (s, 0.17H), 6.46 (s, 0.33H), 7.30–8.52 (m, 7H), 8.78 (s, 1H), 9.22 (d, 0.66H, J=8.27), 9.24 (d, 0.34H, J=8.39) SIMS (m/z); 568 (M+1)$^+$

EXAMPLE 10

The same process as described in Example 3 was repeated, except that 162 mg of Compound (L) as obtained in Reference Example 10 was used in place of Compound (e), to obtain 99 mg (yield: 59%) of Compound No. 8.

$^1$NMR (DMSO-d$_6$) δ(ppm); 4.24 (S, 0.35H), 4.26 (s, 0.3H), 4.48 (s, 0.2H), 4.51 (s, 0.15H), 7.30–8.52 (m, 7H), 8.78 (s, 0.65H), 8.79 (s, 0.35H), 9.22 (d, 0.65H, J=7.56) SIMS (m/z); 623 (M+1)$^+$

EXAMPLE 11

The same process as described in Example 3 was repeated, except that 142 mg of Compound (m) as obtained in Reference Example 12 was used in place of Compound (e), to obtain 39 mg (yield: 26%) of Compound No. 9.

$^1$HNMR (DMSO-d$_6$) δ(ppm); 5.81–5.99 (m, 3H), 6.43 (s, 0.9H), 6.51 (S, 0.1H), 7.28–8.49 (m, 7H), 9.19 (d, 0.9H, J=7.86) SIMS (m/z); 616 (M+1)$^+$

EXAMPLE 12

The same process as described in Example 3 was repeated, except that 129 mg of Compound (n) as obtained in Reference Example 14 was used in place of Compound (e), to obtain 69 mg (yield: 49%) of Compound No. 10.

$^1$HNMR (DMSO-d$_6$) δ(ppm); 4.35 (s, 1H), 6.87 (s, 1H), 6.96 (dd, 1H, J=5.02, 8.79), 7.29–8.51 (m, 7H), 8.78 (s, 1H), 9.23 (d, 1H, J=7.94) SIMS (m/z); 609 (M+1)$^+$

EXAMPLE 13

466 mg (1 mmol) of staurosporine and 360 mg (3 mmol) of glycolaldehydedimer were dissolved in a mixture of 50 ml of tetrahydrofuran and 5 ml of water. The solution was adjusted to pH 5 to 6 with 3N hydrochloric acid. To the solution was added 188 mg (3 mmol) of sodium cyanoborohydride and the mixture was stirred for 2 hours. The reaction mixture was washed with saturated aqueous sodium bicarbonate and dried over anhydrous sodium sulfate. The solvent was evaporated, and the residue was purified by silica gel column chromatography (eluent: 5/95 methanol/chloroform) to obtain 460 mg (yield: 90%) of an intermediate compound.

The intermediate compound $^1$HNHR(DMSO-d$_6$) δ(ppm); 4.99 (s, 2H), 6.86 (dd, 1H, J=3.43, 8.87), 7.27–8.07 (m, 7H), 8.54 (s, 1H), 9.30 (d, 1H, J=7.78). SIMS (m/z); 511 (M+1)$^+$ 300 mg of the intermediate compound obtained above was dissolved in a mixture of 20 ml of dimethylsulfoxide and 6.6 ml of 0.5N sodium hydroxide and the solution was stirred at room temperature overnight. The reaction mixture was diluted with tetrahydrofuran, washed with brine, and dried over anhydrous sodium sulfate. The solvent was evaporated and the residue was purified by silica gel column chromatography to obtain 140 mg (yield: 45%) of a 1:1 mixture of α-form and β-form of Compound No. 1. Each form was isolated from each other by HPLC (eluent: 1/20/80 28% aqueous ammonia/water/methanol).

(1-α)

$^1$HNMR (DMSO-d$_6$) δ(ppm); 2.149 (s, 3H), 2.403 (s, 3H), 4,253 (br, s, 1H), 6,436 (s, 2H), 6,844 (dd, 1H, J=3.6, 8.9), 7.282–8.454 (m, 7H), 8.763 (s, 1H), 9,240 (dd, 1H, J=1.0, 7.9) SIMS (m/z); 527 (M+1)$^+$ (1-β)

$^1$HNMR (DMSO-d$_6$) δ(ppm); 2.202 (s, 3H), 2.397 (s, 3H), 2.803 (m, 1H), 4.256 (br. s, 1H), 6.429 (s, 2H), 6.844 (dd, 1H, J=4.1, 9.0), 7.281–8.508, (m, 7H), 8.768 (s, 1H), 9.244 (dd, 1H, J=1.0, 7.9) SIMS (m/z); 527 (M+1)$^+$ Reference Examples are given below, and the structures of the starting compounds as obtained in Reference Examples are shown in the following Table 6.

TABLE 6

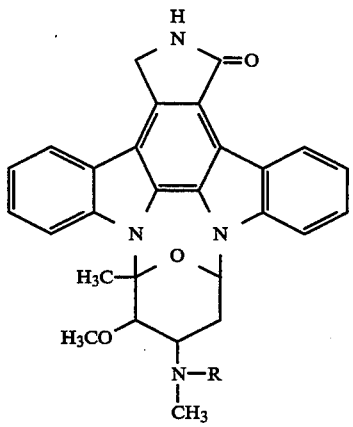

| Reference Example No. | Compound No. | —R |
|---|---|---|
| 1 | e | —(CH₂)₂OH |
| 2 | f | —CH₂CH(OH)CH₂OH |
| 3 | g | —(CH₂)₃COOH |
| 4 | a | —(CH₂)₂OCOO—C₆H₄—NO₂ |
| 5 | h | —(CH₂)₂OCO—N(piperazine)N—CH₃ |
| 6 | i | —CO(CH₂)₂COOH |
| 7 | b | —COCH₂Cl |
| 8 | j | —COCH₂—N(morpholine)O |
| 9 | k | —COCH₂N(CH₃)₂ |
| 10 | L | —COCH₂—N(piperazine)N—CH₃ |
| 11 | c | —CO—C₆H₃(NO₂)₂ (2,4-dinitro) |
| 12 | m | —CO—C₆H₃(NH₂)₂ |
| 13 | d | —COO—C₆H₄—NO₂ |

TABLE 6-continued

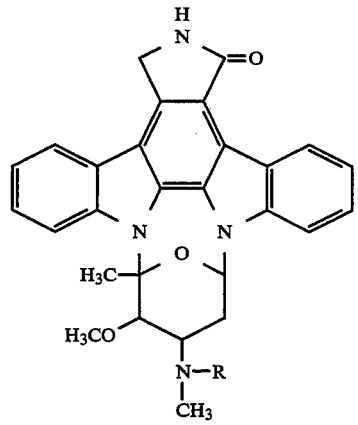

| Reference Example No. | Compound No. | —R |
|---|---|---|
| 14 | n | —CO—N(piperazine)N—CH₃ |

REFERENCE EXAMPLE 1

466 mg (1 mmol) of staurosporine and 360 mg (3 mmol) of glycolaldehydedimer were dissolved in 50 ml of THF and 5 ml of water and the solution was adjusted to pH from 5 to 6 with 3N hydrochloric acid. To the resulting solution was added 188 mg (3 mmol) of sodium cyanoborohydride and stirred for 2 hours at room temperature. The reaction solution was washed with saturated aqueous sodium bicarbonate and dried over anhydrous sodium sulfate. Then, the solvent was evaporated, and the residue was purified by silica gel column chromatography (5/95 methanol/chloroform) to obtain 460 mg (yield: 90%) of Compound (e).

$^1$HNMR (DMSO-$d_6$) δ(ppm); 4.99 (s, 2H), 6.86 (dd, 1H, J=3.43, 8.87), 7.27–8.07 (m, 7H), 8.54 (s, 1H), 9.30 (d, 1H, J=7.78) SIMS (m/z): 511 (M+1)⁺

REFERENCE EXAMPLE 2

In the same manner as described in Reference Example 1, 528 mg (yield: 98%) of Compound (f) was obtained from 466 mg (1 mmol) of staurosporine and 870 mg (3 mmol) of glycolaldehydedimer.

$^1$HNMR (DMSO-$d_6$) δ(ppm); 4.98 (s, 2H), 6.87 (dd, 1H, J=3.44, 9.18), 7.27–8.07 (m, 7H), 8.53 (s, 1H), 9.30 (d, 1H, J=7.89) SIMS (m/z); 541 (M+1)⁺

REFERENCE EXAMPLE 3

In the same manner as described in Reference Example 1, 53 mg (yield: 92%) of Compound (g) was obtained from 47 mg (0.1 mmol) of staurosporine and 130 μl (0.2 mmol) of succinic semialdehyde.

$^1$HNMR (DMSO-$d_6$) δ(ppm); 4.98 (s, 2H), 6.87 (hr. d, 1H, J=6.25), 7.28–8.06 (m, 7H), 8.54 (s, 1H), 9.30 (d, 1H, J=7.89)

REFERENCE EXAMPLE 4

484 mg (0.95 mmol) of Compound (e) as obtained in Reference Example 1 and 382 mg (1.9 mmol) of nitrophenyl chloroformate were dissolved in 25 ml of THF, and 0.26 ml of triethylamine was added thereto and stirred for 3 hours under ice-cooling. The reaction mixture was washed with saturated aqueous sodium bicarbonate and brine, and dried over anhydrous sodium sulfate. Then, the solvent was evaporated, and the residue was purified by silica gel column chromatography (10/90 acetone/chloroform) to obtain 394 mg (yield: 86%) of Compound (a).

$^1$HNMR (DMSO-$d_6$) δ(ppm); 2.12 (s, 3H), 2.42 (s, 3H), 2.61 (s, 3H), 3.95 (t, 1H, J=5.4), 4.97 (s, 2H), 6.86 (dd, 1H, J=3.4, 8.3), 6.92–8.30 (m, 11H), 8.53 (s, 1H), 9.30 (d, 1H, J=8.0) SIMS (m/Z); 676 (M+1)+

REFERENCE EXAMPLE 5

168 mg (0.26 mmol) of Compound (a) and 88 μl (0.79 mmol) of N-methylpiperazine were dissolved in 15 ml of chloroform, and 0.11 ml (0.79 mmol) of triethylamine was added thereto and stirred overnight. The reaction mixture was washed with saturated aqueous sodium bicarbonate, water and brine in order, and dried over anhydrous sodium sulfate. Then, the solvent was evaporated, and the residue was purified by silica gel column chromatography (3/97 methanol chloroform) to obtain 77 mg (yield: 46%) of Compound (h).

$^1$HNMR (DMSO-$d_6$) δ(ppm); 2.10 (s, 3H), 2.41 (s, 3H), 2.60 (s, 3H), 3.76 (m, 2H), 4.24 (s, 2H), 4.98 (s, 2H), 6.85 (dd, 1H, J=3.42, 8.48), 7.27–8.05 (m, 7H), 8.53 (s, 1H), 9.30 (d, 1H, J=7.84) SIMS (m/z); 637 (M+1)+

REFERENCE EXAMPLE 6

14 mg (0.03 mmol) of staurosporine and 6 mg (0.06 mmol) of succinic acid anhydride were dissolved in 0.2 ml of DMF, and 2 mg of dimethylaminopyridine was added thereto and stirred for 4 hours at room temperature. The reaction mixture was diluted with CHCl$_3$, washed with 5% aqueous hydrochloric acid, water and brine in order, and dried over anhydrous sodium sulfate. Then, the solvent was evaporated, and the residue was purified by silica gel column chromatography (10/90 methanol/chloroform) to obtain 16.6 mg (yield: 98%) of Compound (i).

$^1$HNMR (CDCl$_3$/CD$_3$OD 10/1) δ(ppm); 4.00 (d, 1H, J=2.20), 4.96 (s, 2H), 6.61 (m, 1H), 7.17–7.98 (m, 7H), 8.53 (s, 1H), 9.35 (d, 1H, J=6.59) SIMS (m/z); 566 (M+1)+

REFERENCE EXAMPLE 7

932 mg of staurosporine was dissolved in 10 ml of pyridine, and 0.64 ml of chloroacetyl chloride was added thereto and stirred for 8 hours under ice-cooling. The reaction mixture was diluted with chloroform, washed with 1N hydrochloric acid, saturated aqueous sodium bicarbonate and brine in order, and dried over anhydrous sodium sulfate. Then, the solvent was evaporated, and the residue was purified by silica gel column chromatography (10/90 methanol/chloroform) to obtain 184 mg (yield: 18%) of Compound (b).

$^1$HNMR (DMSO-$d_6$) δ(ppm); 5.01 (s, 2H), 7.03–7.08 (m, 1H), 7.28–8.29 (m, 7H), 9.31 (d, 1H, J=8.06) SIMS (m/z); 543 (M+1)+

REFERENCE EXAMPLE 8

200 mg (0.37 mmol) of Compound (b) and 0.16 ml (1.85 mmol) of morpholine were dissolved in 20 ml of chloroform, and 0.26 ml (1.85 mmol) of triethylamine and 0.32 ml (1.85 mmol) of diisopropylethylamine were added thereto and stirred for 2 days. The reaction mixture was washed with brine and dried over anhydrous sodium sulfate. Then, the solvent was evaporated, and the residue was purified by silica gel column chromatography (5/95 methanol/ethyl acetate) to obtain 186 mg (yield: 85%) of Compound (j).

$^1$HNMR (DMSO-$d_6$) δ(ppm); 2.35 (s, 2.1H), 2.44 (s, 0.9H), 2.62 (s, 0.9H), 2.66 (s, 0.9H), 2.78 (s, 2.1H), 2.88 (s, 2.1H), 4.24, 4.49 (2xs, 2H), 5.00 (s, 2H), 7.00 (dd, 0.3H, J=5.76, 7.83), 7.03 (dd, 0.7H, J=6.74, 8.32), 7.28–8.08 (m, 7H), 8.55 (s, 1H), 9.28 (d, 0.7H, J=7.74). SIMS (m/z); 594 (M+1)+

REFERENCE EXAMPLE 9

In the same manner as described in Reference Example 8, 190 mg (yield: 95%) of Compound (k) was obtained from 200 mg (0.37 mmol) of Compound (b) and 0.66 ml (7.37 mmol) of 50% aqueous dimethylamine.

$^1$HNMR (DMSO-$d_6$) δ(ppm); 4.24, 4.38 (2xbr. s, 1H), 5.00 (s, 2H), 6.98 (dd, 0.31H, J=5.12, 9.05), 7.03 (dd, 0.69H, J=6.68, 8.48), 7.28–8.08 (m, 7H), 8.56 (s, 1H), 9.29 (d, 0.69H, J=8.07) SIMS (m/z); 552 (M+1)+

REFERENCE EXAMPLE 10

In the same manner as described in Example 8, 181 mg (yield: 81%) of Compound (L) was obtained from 200 mg (0.37 mmol) of Compound (b) and 0.21 ml (1.85 mmol) of N-methylpiperazine.

$^1$HNMR (DMSO-$d_6$) δ(ppm); 4.24 (m, 0.75H), 4.48 (m, 0.25H), 5.00 (s, 2H), 6.98 (dd, 0.25H, J=5.66, 8.64), 7.03 (dd, 0.75H, J=6.65, 8.42), 7.28–8.09 (m, 7H), 8.56, 8.57 (2xs, 1H), 9.28, 9.30 (2xd, 1H, J=7.44) SIMS (m/z); 607 (M+1)+

REFERENCE EXAMPLE 11

200 mg of staurosporine and 297 mg (1.29 mmol) of 3,5-dinitrobenzoylchloride were dissolved in 20 ml of methylene chloride, and 1.2 ml (8.6 mmol) of triethylamine was added thereto and stirred for 0.5 hour under ice-cooling. The reaction mixture was diluted with CHCl$_3$, washed with water and brine in order, and dried over anhydrous sodium sulfate. Then, the solvent was evaporated, and the residue was purified by silica gel column chromatography (3/97 methanol/chloroform) to obtain 249 mg (yield: 88%) of Compound (c).

$^1$HNMR (DMSO-$d_6$) δ(ppm); 2.47 (s, 3H), 2.64 (s, 3H), 2.78 (s, 3H), 5.00 (s, 2H), 5.14 (d, 1H, J=11.3), 7.11 (m, 1H), 7.29–8.98 (m, 10H), 9.30 (d, 1H, J=8.2) SIMS (m/z); 661 (M+1)+

REFERENCE EXAMPLE 12

200 mg (0.3 mmol of Compound (c) was dissolved in 4 ml of DMF, and 130 mg of 10% Pd/C was added thereto and stirred for 3 hours under hydrogen atmosphere at room temperature. The reaction mixture wad filtered through sellaite, and the solvent was evaporated. The residue was purified by silica gel column chromatography (5/95 methanol/chloroform) to obtain 150 mg (yield: 79%) of Compound (m).

$^1$HNMR (DMSO-$d_6$) δ(ppm); 5.00 (s, 2H), 5.78–5.97 (m, 3H), 7.28–8.08 (m, 7H), 8.56 (s, 1H), 9.29 (d, 1H, J=7.95) SIMS (m/z); 601 (M+1)+

REFERENCE EXAMPLE 13

233 mg of staurosporine and 301 mg of nitrophenyl chloroformate were dissolved in 20 ml of chloroform, and 0.21 ml (1.5 mmol) of triethylamine was added thereto and stirred for 4 days under ice-cooling. The reaction mixture was washed with saturated aqueous sodium bicarbonate and brine in order, and dried over anhydrous sodium sulfate. Then, the solvent was evaporated, and the residue was purified by silica gel column chromatography (10/90 acetone/chloroform) to obtain 265 mg (yield: 84%) of Compound (d).

$^1$HNMR (DMSO-d$_6$) δ(ppm); 2.77 (s, 3H), 5.01 (s, 2H), 7.05 (m, 1H), 7.30–8.09 (m, 7H), 8.59 (s, 1H), 9.31 (d, 1H, J=7.92). SIMS (m/z); 632 (M+1)$^+$

REFERENCE EXAMPLE 14

175 mg (0.27 mmol) of Compound (d) and 15 ml (1.4 mmol) of N-methylpiperazine were dissolved in 5 ml of DMF, and 0.2 ml (1.4 mmol) of triethylamine was added thereto and stirred for 5.5 hours at 70° C. The reaction mixture was diluted with chloroform, washed with saturated aqueous sodium bicarbonate, water and brine in order, and dried over anhydrous sodium sulfate. Then, the solvent was evaporated, and the residue was purified by silica gel column chromatography (10/90 methanol/chloroform) to obtain 145 mg (yield: 90%) of Compound (n).

$^1$HNMR (DMSO-d$_6$) δ(ppm); 2.39 (s, 3H), 2.59 (s, 3H), 2.66 (s, 3H), 4.36 (d, 1H, J=0.78), 4.42 (ddd, 1H, J=2.26, 4.88, 12.87), 5.00 (s, 2H), 6.98 (dd, 1H, J=5.22, 8.84), 7.28–8.07 (m, 7H), 8.56 (s, 1H), 9.29 (d, 1H, J=7.91) SIMS (m/z); 593 (M+1)$^+$

What is claimed is:

1. A process for producing a staurosporine derivative represented by Formula (I):

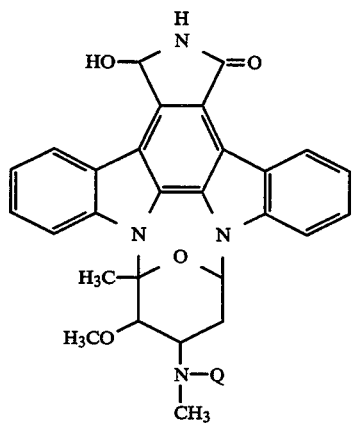

wherein:

Q represents hydrogen or —X—(CH$_2$)$_m$—Y—(CH$_2$)$_n$—Z wherein:

X represents a single bond or —CO—

Y represents a single bond or —CH(OH)—

Z represents hydroxy, O C O N R$^1$R$^2$, in which each of R$^1$ and R$^2$ independently represents hydrogen or lower alkyl, or R$^1$ and R$^2$, combined together with the nitrogen atom adjacent thereto, form a heterocyclic group selected from the group consisting of pyrrolidinyl, imidazolidinyl, pyrazolidinyl, piperidino, morpholino, piperazinyl, N-methylpiperizinyl, indolinyl and isoindolinyl, carboxyl, N R$^3$ and R$^4$, in which each of R$^3$ and R$^4$ independently represents hydrogen or lower alkyl, or R$^3$ and R$^4$, combined together with the nitrogen atom adjacent thereto, form a heterocyclic group selected from the group consisting of pyrrolidinyl, imidazolidinyl, pyrazolidinyl, piperidino, morpholino, piperazinyl, N-methylpiperizinyl, indolinyl and isoindolinyl, or, aryl which is optionally substituted with 1 to 3 substituents independently selected from the group consisting of lower alkyl, lower alkoxy, amino, halogen and nitro, each of m and n independently represents an integer from 0 to 6, or a pharmaceutically acceptable salt thereof, which comprises oxidizing a compound represented by the formula (II)

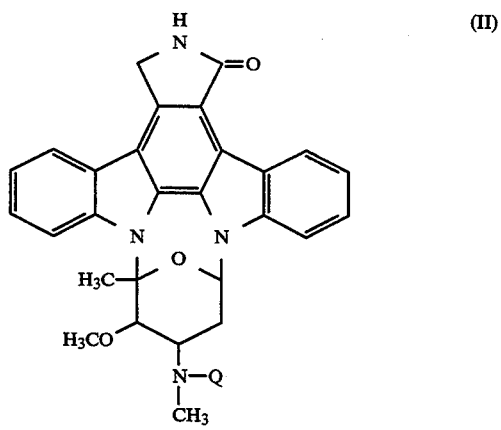

wherein Q has the same meaning as previously defined, with dimethylsulfoxide (DMSO) and an aqueous alkaline solution.

2. A staurosporine derivative represented by Formula (I-1):

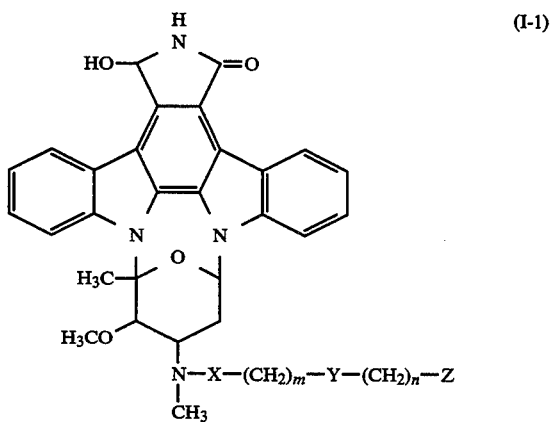

wherein:

X represents a single bond or —CO—

Y represents a single bond or —CH(OH)—

Z represents hydroxy,

O C O N R$^1$R$^2$, in which each of R$^1$ and R$^2$ independently represents hydrogen or lower alkyl, or R$^1$ and R$^2$, combined together with the nitrogen atom adjacent thereto, form a heterocyclic group selected from the group consisting of pyrrolidinyl, imidazolidinyl, pyrazolidinyl, piperidino, morpholino, piperazinyl, N-methylpiperizinyl, indolinyl and isoindolinyl, carboxyl, N R$^3$ and R$^4$, in which each of R$^3$ and R$^4$ independently represents hydrogen or lower alkyl, or R$^3$ and R$^4$, combined together with the nitrogen atom adjacent thereto, form a heterocyclic group selected from the group consisting of pyrrolidinyl, imidazolidinyl, pyrazolidinyl, piperidino, morpholino, piperazinyl, N-methylpiperizinyl, indolinyl and isoindolinyl, or, aryl which is optionally substituted with 1 to 3 substituents independently selected from the group consisting of lower alkyl, lower alkoxy, amino, halogen and nitro, each of m and n independently represents an integer from 0 to 6, or a pharmaceutically acceptable salt thereof.

3. The staurosporine derivative according to claim 2, wherein both X and Y are a single bond, Z is hydroxy, and one of m and n is 0 and the other is 2, or both of m and n is one.

4. A pharmaceutical composition comprising, as an active ingredient, an effective amount of the staurosporine derivative as defined in claim 2, and a pharmaceutically acceptable carrier.

* * * * *